United States Patent [19]

House

[11] Patent Number: 4,500,740
[45] Date of Patent: Feb. 19, 1985

[54] HYDROLYSIS OF WATER-INSOLUBLE ORGANIC HALIDES

[75] Inventor: David W. House, Arlington Heights, Ill.

[73] Assignee: UOP Inc., Des Plaines, Ill.

[21] Appl. No.: 567,204

[22] Filed: Dec. 30, 1983

[51] Int. Cl.$^3$ .............................................. C07C 37/02
[52] U.S. Cl. ..................................... 568/796; 568/739; 568/770; 568/778; 568/797
[58] Field of Search ............... 568/796, 797, 739, 769, 568/770, 795, 778

[56] References Cited

U.S. PATENT DOCUMENTS 2,129,907  9/1938  Britton ............................... 568/797
2,523,707  9/1950  Miller ................................. 568/796
2,988,573  6/1961  Siebentritt et al. ................. 568/797

Primary Examiner—Werren B. Lone
Attorney, Agent, or Firm—William H. Page, II; Eugene I. Snyder

[57] ABSTRACT

Secondary and tertiary alkyl halides, benzyl halides, and activated phenyl halides may be hydrolyzed in a 2-step procedure in good yield and under relatively mild conditions. The halide first is heated with dimethyl sulfoxide so as to form an intermediate or complex which is subsequently hydrolyzed with great facility upon contact with water, even at room temperature. The process is particularly applicable to water-insoluble organic halides.

4 Claims, No Drawings

HYDROLYSIS OF WATER-INSOLUBLE ORGANIC HALIDES

BACKGROUND OF THE INVENTION

The hydrolysis of organic halides is an important source of alcohols and, in some cases, phenols. For example, the hydrolysis of secondary and tertiary alkyl halides, generally readily available via addition of a hydrogen halide to olefins, is a principal source of alcohols, and hydrolysis of some activated aryl halides similarly afford phenols.

Where the halide is water-insoluble an organic cosolvent often is employed in the hydrolysis procedure. But the use of an organic cosolvent often is procedurally inconvenient and is sometimes accompanied by side reactions which appreciably decrease the amount of alcohol or phenol formed. There is, therefore, an impetus for a hydrolytic process which is homogeneous and which avoids the disadvantages attending use of a cosolvent.

SUMMARY OF THE INVENTION

An object of this invention is to afford a method of hydrolyzing water-insoluble organic halides in good yields. A more specific object is to disclose a process for hydrolyzing water-insoluble organic halides under mild reaction conditions so as to minimize side reactions often accompanying such hydrolysis. An embodiment comprises the reaction of a secondary or tertiary alkyl halide with dimethyl sulfoxide followed by contact of the reaction mixture with at least a stoichiometric amount of water and recovering the product formed thereby.

DESCRIPTION OF THE INVENTION

The invention herein is a method of hydrolyzing a water-insoluble alkyl, arylmethyl, or activated phenyl halide, other than a fluoride, comprising heating said halide in dimethyl sulfoxide so as to effect a reaction between the halide and dimethyl sulfoxide, contacting the resulting mixture with at least a stoichiometric quantity of water, and recovering the hydrolysis product formed thereby. The invention rests on the observation that the halides of this invention form a complex or intermediate with dimethyl sulfoxide which is exceedingly labile to hydrolysis.

The halides which can be used in the practice of this invention are water-insoluble organic chlorides, bromides, and iodides. Organic fluorides sometimes may be used in this invention but not necessarily with equivalent results. In particular, many organic fluorides are resistant to hydrolysis and, therefore, are not included as suitable substrates in the practice of this invention. Chlorides and bromides are especially desirable because of their generally greater availability.

Among the organic halides which may be used in this invention are alkyl halides where the alkyl moiety is a secondary or tertiary alkyl moiety. Although the alkyl portion is not limited as to carbon content for the success of this invention, as a practical matter the alkyl portion contains up to about 20 carbon atoms. Examples of suitable alkyl moieties include isopropyl, sec-butyl, tert-butyl, 3-pentyl, 2-pentyl, 3-methyl-2-pentyl, 2-methyl-2-pentyl, and secondary and tertiary hexyl, heptyl, octyl, nonyl, decyl, undecyl, dodecyl, tridecyl, tetradecyl, pentadecyl, hexadecyl, heptadecyl, octadecyl, nonadecyl, and eicosyl moieties.

The alkyl moieties of this invention also may bear substituents which are otherwise inert under the reaction conditions. Especially important is an aryl substituent on the alkyl chain. Examples of suitable aralkyl moieties include 1-phenylethyl, 1-phenyl-3-butyl, 3-phenyl-2-butyl, and all other phenyl substituted alkyl moieties where the alkyl portion otherwise conforms to the foregoing description. Because benzyl-type halides form an exception to the generality that primary halides are unsuitable substrates in the practice of this invention, arylmethyl halides are included among the organic halides which may be so utilized. Some examples of arylmethyl moities are benzyl, 1-naphthylmethyl, 2-naphthylmethyl, 1-anthracenylmethyl, 2-anthracenylmethyl, 9-anthracenylmethyl, and so forth.

Activated aryl halides are another class of organic halides which may be hydrolyzed by the method described herein. Ordinarily aryl halides are not readily hydrolyzed and are not suitable for practice in this invention. However, where the aryl moiety bears one or more strongly electron withdrawing groups at the 2- or 4-position relative to the halogen, the halogen may become sufficiently activated to undergo hydrolysis according to the procedure herein. Examples of suitable groups include the trialkylammonium group, nitro, nitrilo, carboxyl, carbonyl, fluorine, and nitroso groups. Among these the nitro group is especially important. Examples of activated aryl halides include 2-nitrochlorobenzene, 4-nitrobromobenzene, 2,4-dinitroiodobenzene, 2,4,6-trinitrochlorobenzene, 4-trimethylammoniumchlorobenzene, 2-cyanobromobenzene, 4-fluoro-2-carboxychlorobenzene, 2,4-bis(methylcarbonyl)bromobenzene, and so forth.

The organic halide is then heated in dimethyl sulfoxide either as a solution or suspension so as to effect reaction between the halide and dimethyl sulfoxide. Heating may be done at a temperature up to about the onset of decomposition of dimethyl sulfoxide, which is approximately 100° C., but can be performed at a lower temperature if longer reaction times are used. The mixture generally is heated at a temperature between about 50° and about 100° C. As stated above, the reaction time is a function of reaction temperature, but usually is not more than about 0.5 hours at about 100° C.

After the halide and dimethyl sulfoxide are heated for an appropriate time the mixture usually is cooled prior to water addition, although this is not absolutely necessary. However, addition of water to a cooled reaction mixture ensures relatively mild hydrolytic conditions and tends to minimize side reactions. By "side reactions" are meant those reactions occurring other than hydrolysis. Addition of a stoichiometric amount of water, based on the organic halide used, is sufficient for the success of this invention. However, an excess of water, and generally a large excess, is employed for convenience and because recovery of the hydrolysis product often entails diluting the dimethyl sulfoxide reaction mixture with a copious quantity of water. Hydrolysis generally is complete in minutes at room temperature, but to ensure complete reaction a time up to about 1 hour may be employed.

The hydrolysis product formed, i.e., an alcohol or phenol, is then recovered by suitable means. For example, some of the lower alcohols can be recovered by distillation from the reaction medium. In other cases the reaction medium can be diluted with copious quantities of water followed by extraction with a relatively low boiling organic solvent to selectively remove the hydrolysis product from the aqueous solution. After extraction the solvent may be removed, as by evaporation, and the residue collected is the extracted alcohol or phenol.

The example given below is merely illustrative of my invention and is not intended to limit it thereby.

EXAMPLE

Preparation of 1,4-bis(1'-hydroxyethyl)benzene

In a 100 ml flask equipped with a reflux condenser and magnetic stirring bar a solution of 1.00 g (3.42 mmol) 1,4-bis(1'-bromoethyl)benzene in 50 ml dimethylsulfoxide was heated to 100° C. for 0.5 hours. Methylene chloride (50 ml) was added to the cooled solution, and the mixture extracted with 3 75-ml portions water to simultaneously effect hydrolysis and remove dimethylsulfoxide. The methylene chloride layer was dried ($MgSO_4$), filtered, and solvent was evaporated under reduced pressure to afford 1,4-bis(1'-hydroxyethyl)benzene in about 68% yield.

The following experiments were performed for comparative purposes using 1,4-bis(1'-bromoethyl)benzene as the reactant in all cases. A heterogeneous reaction mixture of chloroform (20 ml) and either 10% or 50% aqueous sodium hydroxide (45 ml) at 70° C. for one hour afforded no alcohol. A solution of 2.00 g (6.84 mmol) dibromide in 20 ml 2M ethanolic KOH and 50 ml water at 70° C. for 30 minutes afforded reactant containing approximately equal amounts of ether (a mixture of diether and hydroxyether) and diol. A mixture, initially heterogeneous in dibromide but becoming homogeneous upon heating, of 1.00 g (3.42 mmol) dibromide in 100 ml of a 3:1 acetone-water solvent system containing 0.30 g (3.61 mmol) sodium carbonate was heated at reflux for 2 hours to afford 0.51 g (90%) of material identified as 1,4-bis(1'-hydroxyethyl)benzene by NMR and IR spectroscopy.

What is claimed is:

1. A method of hydrolyzing a water-insoluble organic halide, other than a fluoride, where the organic halide is a secondary or tertiary alkyl halide whose alkyl moiety contains up to about 20 carbon atoms, an arylmethyl halide, or an activated aryl halide where said aryl moiety bears at the 2- or 4-position relative to the halogen at least one strongly electron withdrawing moiety selected from the group consisting of trialkylammonium, nitro, nitrilo, carboxyl, carbonyl, fluorine, and nitroso, comprising heating the organic halide in dimethylsulfoxide at a temperature between about 50° and 100° C., contacting the resulting mixture with at least a stoichiometric quantity of water, and recovering the hydrolysis product formed thereby.

2. The method of claim 1 where the activated aryl halide is a nitrophenyl halide.

3. The method of claim 1 where the halide is a chloride.

4. The method of claim 1 where the halide is a bromide.

* * * * *